United States Patent [19]

Buck

[11] Plant 4,653

[45] Feb. 17, 1981

[54] GERANIUM PLANT NAMED SUPER-WALTZTIME

[75] Inventor: Griffith J. Buck, Ames, Iowa

[73] Assignee: Iowa State University Research Foundation, Inc., Ames, Iowa

[21] Appl. No.: 112,114

[22] Filed: Jan. 14, 1980

[51] Int. Cl.[3] ..... A01H 5/00

[52] U.S. Cl. ..... Plt./68

[58] Field of Search ..... PLT./68

*Primary Examiner*—James R. Feyrer

*Attorney, Agent, or Firm*—Chas. W. Rummler

[57] ABSTRACT

A new cultivar of geranium plant distinguished by flowers that have a delicate pink coloration that intensifies under high temperature and light intensities, the very large size of its inflorescence clusters, and a continuous and abundant flowering habit throughout the year with adequate length of photoperiod. This new plant is more compact and free branching and, because of its greater number of stems and a consistent tendency to produce flowers on a 2–4 node cycle, has a greater flowering potential than its predecessors.

1 Drawing Figure

BACKGROUND OF THE NEW PLANT

My new geranium plant originated as a seedling of "Skylark" × "Waltztime", both unpatented, the cross having been made by me at Iowa State University at Ames, Iowa, in the course of breeding efforts carried on by me since 1956 with the object of developing improved geranium cultivars having better adaptability to the summer climates of the upper Midwest of the United States, including tolerance to the high summer night temperatures and humidity and a tolerance to *Botrytis cinerea* infection. This new plant was selected by me for propagation because of the color character of its inflorescence and its apparent fulfillment of my principal objectives and propagation under my direction through successive generations by means of cuttings at the Iowa State University horticultural greenhouses has shown that its distinctive and novel characteristics hold true from generation to generation and appear to be firmly fixed. Propagation of this new geranium plant for the commercial market is now being done by meristem culture and cuttings at Connellsville, Pa.

DESCRIPTION OF THE DRAWING

My new geranium plant is illustrated by the accompanying full color photograhic drawing which shows a potted plant in full bloom, the colors shown being as nearly true as it is reasonably possible to obtain by conventional commercial photographic procedures.

DESCRIPTION OF THE NEW PLANT

The following is a detailed description of my new geranium cultivar with color designations according to The R.H.S. Colour Chart published by The Royal Horticultural Society of London, England, the data having been obtained from observations of the plants of this new cultivar grown in the horticultural greenhouses of Iowa State University at Ames, Iowa.

THE PLANT

Origin: Seedling.

Parentage:

*Seed parent.*—"Skylark" (unpatented).

*Pollen parent.*—"Waltztime" (unpatented).

Classification:

*Botanic.*—Pelargonium × Hortorim, Bailey.

*Commercial.*—Garden geranium.

Form: Bush.

Height: 25 to 40 cm. (25 cm. as a 4 inch pot plant).

Growth: Compact and vigorous.

Habit: Erect and free-branching with sturdy, strong stems.

Foliage:

*Quantity.*—Abundant.

*Leaves.*—Size—Medium large, about 10 to 11 cm. long × 7.5 to 9.5 cm. wide. Shape: Round-cordate with several rounded lobes and serrated margins. Texture: Firm and slightly velvety to the touch. Color: Upper side—138A with central zone of 146B. Under side—138B.

*Petioles.*—Length: 9 to 14 cm.

THE BUD

Size: 14 to 16 mm. long and 9 to 11 mm. wide.

Shape: Pointed ovoid.

Opening: Buds open slowly.

Color:

*When sepals first divide.*—154D.

*When petals begin to unfurl.*—154D suffused with 41C.

Sepals: At first, erect; and later curling back.

*Shape.*—Long-pointed ovate.

*Color.*—Inside—146D. Outside—146C veined with 180A.

Calyx:

*Aspect.*—Hairy.

Peduncle: Strong and erect.

*Length.*—15 to 22 cm.

*Aspect.*—Hairy.

*Color.*—146B.

THE FLOWER

Flowering habit: Continuous and abundant throughout the year with adequate length of photoperiod.

Inflorescence:

*Type.*—Umbel.

*Size.*—Very large.

*Diameter.*—10 to 13 cm.

*Depth.*—6 to 8 cm.

*Shape.*—Semi-globular.

*Number of florets or buds.*—50 to 60.

*Peduncle.*—Sturdy and upright. Length: 15 to 25 cm. Color: 138A.

*Florets.*—Shape: When bloom first opens—Cup-shaped. The cup flattens to saucer-shape as bloom matures. Petals: Number: 9 to 14, including petaloids. Form: Obovate to spatulate. Arrangement: Slightly imbricated. Color: Spring: White lightly suffused and veined with RHS 41C and a suggestion of a basal blotch of RHS 33A. Summer-Fall: White ground suffused with RHS 41C and developing a margin of RHS 42A. 33A at base of petal and extending into upper half of petal. Winter: White suffused with RHS 41C with a basal blotch of RHS 33A. Reverse Side of Petals: White suffused with RHS 154D; tinted and veined with RHS 41C. Petaloids: Number: 1 to 5. Size: 1.5 to 2.0 cm. Color: Same as petals. Pedicel: Length: 2.0 to 3.1 cm. Strength: Good.

Effect of weather: None

Persistence: Florets hang on and dry.

Disease resistance: Tolerant to *Botrytis cinerea* as observed in area where the disease is prevalent.

Lasting quality: 7 days.

REPRODUCTIVE ORGANS

Stamens:

*Anthers.*—5 to 8 in number. Length: 3 to 4 mm. Arrangement: Cylindrical.

*Filaments.*—Length: 5 to 6 mm. Color: White.

*Pollen.*—Color—Reddish-Brown.

Pistils: Number—1.

*Styles.*—8 to 9 mm. long.

*Stigma.*—Color—Red-Brown.

Fruit: Partially fertile.

*Shape.*—Ovoid with a long beak.

*Color at maturity.*—Brownish-Black.

This geranium is similar in growth habit and cultural requirements to the older cultivars "Waltztime" and "Skylark". The flower color is in the same general color range of those cultivars but differs from them in that the color intensifies under high temperatures and high light intensities. This new plant is more compact and free branching, and because of its greater number of stems and a consistent tendency to produce flowers on a 2–4 node cycle, it has a greater flowering potential than the earlier cultivars.

I claim:

1. A new and distinct cultivar of geranium plant substantially as herein shown and described, characterized by a vigorous and much branched growth habit and a continuous and abundant year around flowering under photoperiod culture.

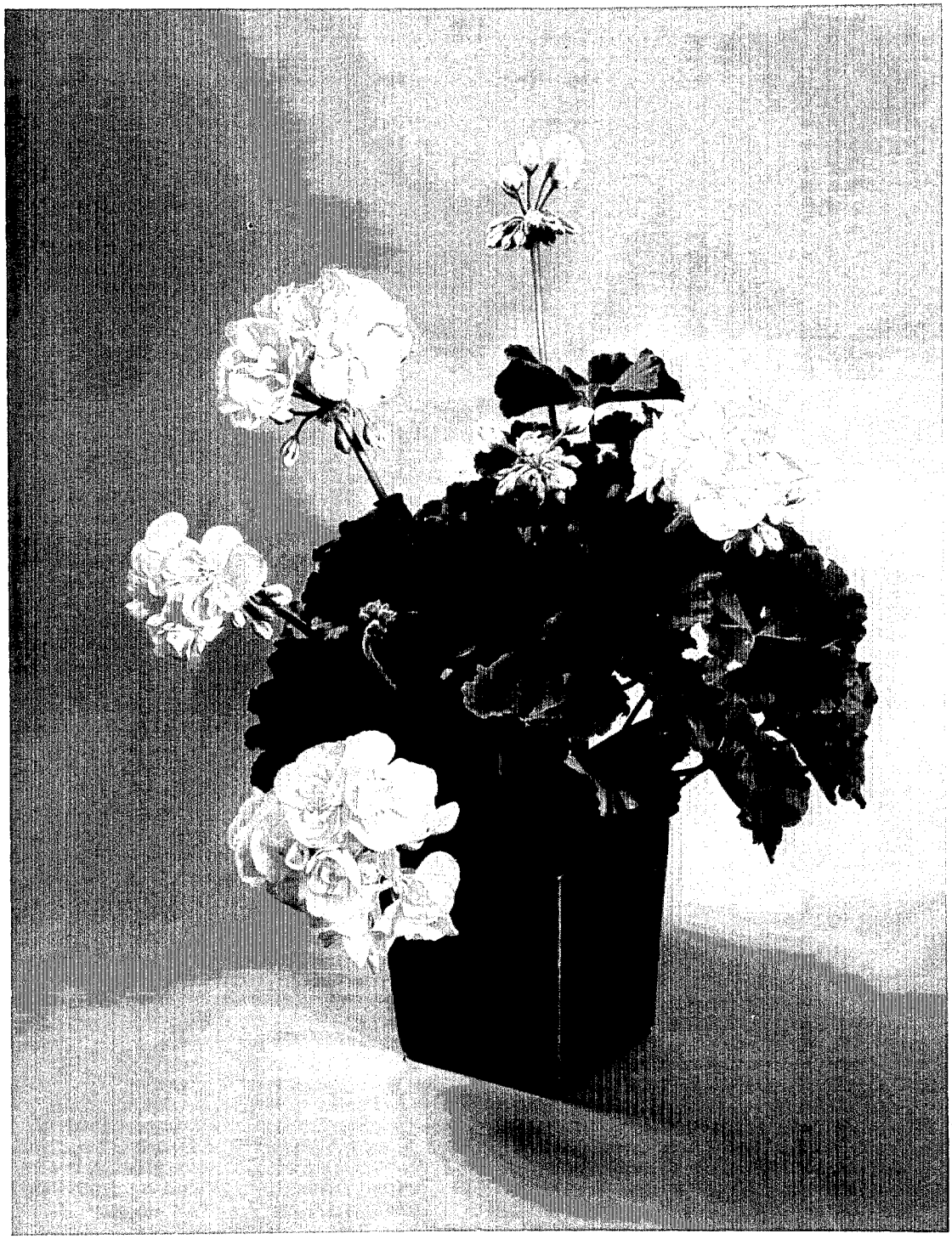

* * * * *